United States Patent
Gray et al.

(10) Patent No.: US 6,195,166 B1
(45) Date of Patent: Feb. 27, 2001

(54) PHOTOREFLECTANCE SPECTRAL ANALYSIS OF SEMICONDUCTOR LASER STRUCTURES

(75) Inventors: Mary L. Gray, Wyomissing, PA (US); Harald F. Hess, San Diego, CA (US); Mark S. Hybertsen, West Orange; Leonard Jan-Peter Ketelsen, Clinton, both of NJ (US)

(73) Assignee: Lucent Technologies, Inc., Murray Hill, NJ (US)

( * ) Notice: Subject to any disclaimer, the term of this patent is extended or adjusted under 35 U.S.C. 154(b) by 0 days.

(21) Appl. No.: 09/305,712

(22) Filed: May 5, 1999

Related U.S. Application Data

(60) Provisional application No. 60/084,855, filed on May 8, 1998.

(51) Int. Cl.$^7$ .................................................. G01N 21/55
(52) U.S. Cl. ............................................. 356/447; 356/448
(58) Field of Search ............................. 356/432 T, 447, 356/448

(56) References Cited

U.S. PATENT DOCUMENTS 5,706,094 * 1/1998 Maris ...................................... 356/432

OTHER PUBLICATIONS

Investigation of Wafer–Sized Quantum Well Laser Structures SPIE vol. 2693, pp. 455–466, No date available.

V.M. Airaksinen, H.K. Lipsanen, "Photoreflectance study of photovoltage effects in GaAs diode structures" Appl. phys. Lett. 60 (17), Apr. 17, 1992.

* cited by examiner

Primary Examiner—Frank G. Font
Assistant Examiner—Amanda Merlino

(57) ABSTRACT

A micro-photoreflectance technique has been developed for performing non-destructive analysis of III–V optoelectronic devices. By using a significantly reduced spot size (for example, 10 micrometers), various compositional features of the device may be analyzed and the Franz-Keldysh oscillations appearing in the micro-photoreflectance wavelength spectra (such as those beyond the barrier/SCL wavelength in an EML structure) may be analyzed to provide information regarding the physical characteristics of the device, such as the electric field and p-i junction placement within an exemplary EML device structure.

7 Claims, 6 Drawing Sheets

PHOTOREFLECTANCE SPECTRAL ANALYSIS OF SEMICONDUCTOR LASER STRUCTURES

Priority of U.S. Provisional Application Ser. No: 60/084,855, filed May 8, 1998 is hereby claimed.

TECHNICAL FIELD

The present invention relates to non-destructive analysis III–V optoelectronic structures and, more particularly, to the use of micro-photoreflectance to characterize the III–V structure and provide information regarding the physical properties of the structure.

BACKGROUND OF THE INVENTION

During the fabrication of III–V optoelectronic devices, it is often beneficial to be able to characterize the physical properties of the various layers forming the device. For example, electro-absorption modulated lasers (EMLs) require a large extinction ratio (e.g., >21.0 dB) in order to provide an acceptable level of performance. The extinction ratio is dependent upon a number of factors, such as the quantum well structure, the width of the active region, and the p-i junction placement. For an optimal extinction ratio, the applied field must be present only across the active region. Further, knowledge of the p-i junction position is critical in preventing over-diffusion of zinc (a p-type dopant in EML devices) into the structure.

In the prior art, correlation of a device parameter such as the extinction ratio with the wafer level material properties has been accomplished by employing Secondary Ion Mass Spectroscopy (SIMS) analysis. With the SIMS analysis, the position and carrier density of the p-type zinc dopant can be monitored with respect to the active region. However, this method is destructive and can only be performed on a sample basis. To date, there has been no method established for monitoring the characteristics of each wafer containing EML devices as they are processed.

SUMMARY OF THE INVENTION

The need remaining in the prior art is addressed by the present invention, which relates to non-destructive analysis of III–V laser structures and, more particularly, to the use of micro-photoreflectance to characterize the structure and provide information regarding the physical properties (such as the placement of the p-i junction) within the optoelectronic device structure.

In accordance with the present invention, conventional photoreflectance apparatus is modified by incorporating various lensing elements to produce an illumination spot size of approximately 10 micrometers (compared to the usual 100 micrometer spot size). Photoreflectance, as a type of modulation spectroscopy, provides wavelength information from, for example, the various quarternary and binary layers of an InGaAsP EML structure, where the small spot size used in the present invention allows for the micro-photoreflectance procedure to recognize compositional changes present for the selectively grown alloy materials. As an exemplary EML structure is scanned with a monochromatic source, the collected wavelength information includes Franz-Keldysh oscillations that follow the barrier and separate confinement layers. An electric field calculation may be made based upon these oscillations to derive the location of the p-i junction in the EML structure.

An additional feature of the present invention is that the use of micro-phtoreflectance can provide information regarding the uniformity of the various materials forming the opto-electronic device structure, since the measured wavelength will vary if the material is not uniform.

An advantage of the use of micro-photoreflectance in association with the present invention is that the process is non-destructive and can therefore be used to characterize each processed wafer.

Other and further advantages of the present invention will become apparent during the course of the following discussion and by reference to the accompanying drawings.

BRIEF DESCRIPTION OF THE DRAWINGS

Referring now to the drawings.

DETAILED DESCRIPTION

The following discussion describes the use of the inventive micro-photoreflectance technique in association with the analysis of an externally modulated laser (EML) structure. It is to be understood that the micro-photoreflectance technique of the present invention may be used to analyze any III–V optoelectronic device, the discussion of an EML device analysis considered to be exemplary only and in no way limiting the scope of the present invention.

Figure 1:
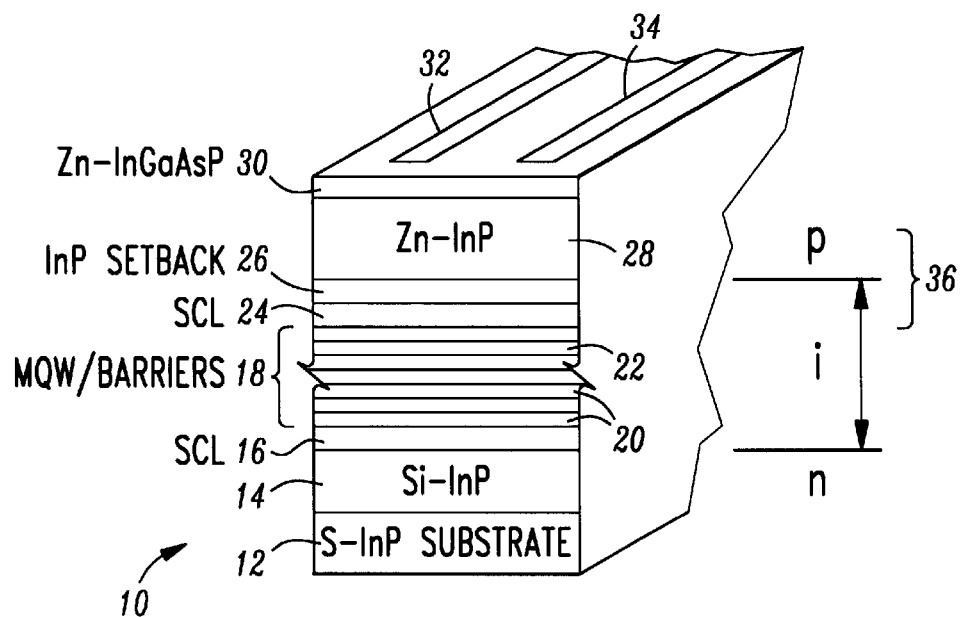
FIG. 1 illustrates an exemplary EML structure that may be analyzed using the photoreflectance technique of the present invention.

FIG. 1 contains, in an exaggerated view, an exemplary EML structure 10 that may be characterized using the micro-photoreflectance technique of the present invention. EML structure 10, which may be grown by MOCVD, comprises an n-type substrate 12 upon which is grown an n-type InP layer 14. A first separate confinement layer 16 (1.26 μm) is subsequently grown above n-type layer 14. As shown in FIG. 1, a multiple quantum well (MWQ) section 18 comprising a number of periods of 1.55 μm wavelength InGaAsP wells 20 and 1.26 μm wavelength barriers 22 is then grown on first SCL 16. In an exemplary embodiment, wells 20 may comprise a thickness of approximately 70 Å and barriers 22 may comprise a thickness of approximately 60 Å. A second separate confinement layer 24 (undoped) is the grown to cover MWQ section 14, as shown. EML structure 10 further comprises an undoped InP setback layer 26, followed by a zinc-doped InP cladding layer 28 and a final, sacrificial InGaAsP zinc-doped layer 30. A pair of silicon dioxide stripes 32,34 are disposed as shown over layer 30. As discussed above, zinc is a relatively rapidly diffusing dopant species, thus influencing the position of the p-i junction 36 within MQW section 18, as depicted by the diagram associated with FIG. 1.

Figure 2:
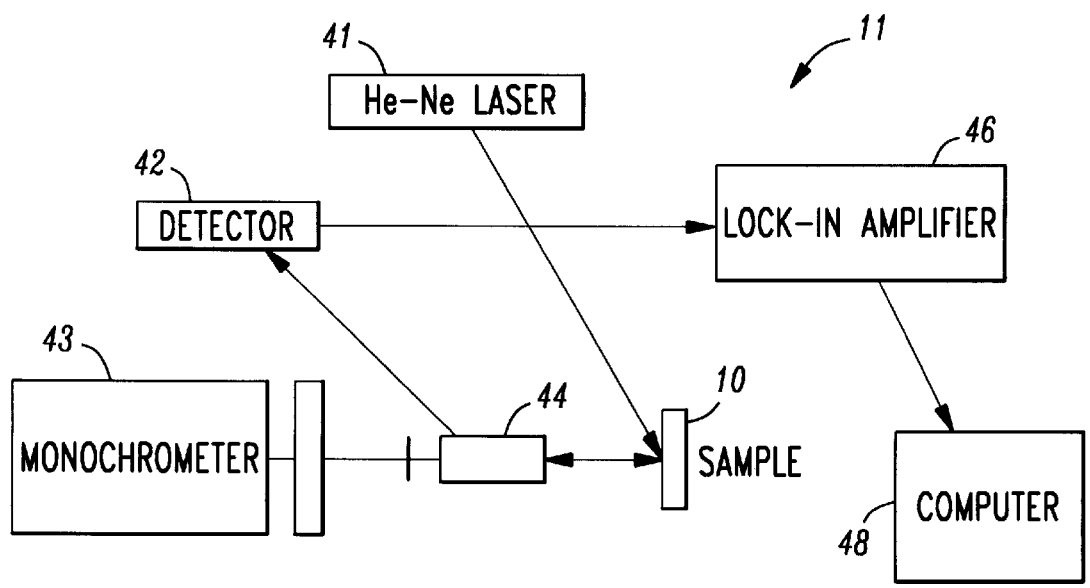
FIG. 2 contains an arrangement of the photoreflectance apparatus that may be used to provide the micro-photoreflectance analysis in accordance with the present invention.

In accordance with the arrangement of the present invention, micro-phtoreflectance arrangement 11, as shown in FIG. 2, may be used to measure the reflected wavelengths from EML. structure 10 (or any other III–V optoelectronic device being studied) so as to characterize the properties of the various layers of EML structure and, importantly, pinpoint the location of p-i junction 36 within the structure. As shown in FIG. 2, micro-photoreflectance arrangement 11 comprises a monochromatic modulation light source 40. In one embodiment light source 40 may comprise a He—Ne laser 41 and monochrometer 43, providing an output wavelength of 6328 Å at a power of approximately 3 mW, modulated at a frequency of approximately 200 Hz. A lightwave detector 42, such as an InGaAs detector, is then use to measure the photoreflected spectra over a predetermined interval, such as 0.7 eV to 1.4 eV. As mentioned above, a significant aspect of the present invention is the use of a relatively small spot size, such as 10 micrometers, so as to allow for reflectance variations across the various materials forming EML structure 10 to be captured and evaluated by detector 42. A lensing arrangement 44, comprising a suitable selection of various lenses and apertures is disposed between monochrometer 43 and EML structure 10 to reduce the conventional 100 micrometer spot size of the He—Ne laser to the preferred 10 micrometer spot size. The output from photodetector 42 is thereafter amplified within a lock-in amplifier 46 and provided as an input to a computer 48 for analyzing the output from photodetector 42.

Figure 3:
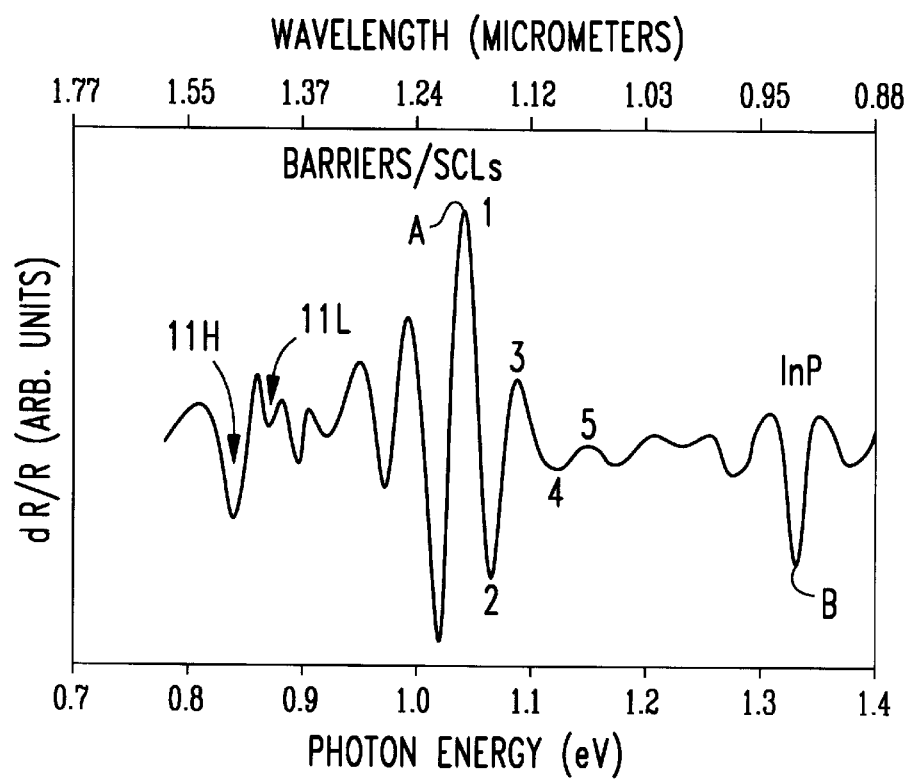
FIG. 3 is a graph of the photoreflectance spectrum obtained from the planar (modulator) region of an EML structure.

A micro-photoreflectance spectrum obtained for the planar region of EML structure 10 is shown in FIG. 3. The change in reflectance is displayed as functions of photon energy (eV) and wavelength (micrometers). The initial photoreflectance features appearing between 0.8 eV and 1.0 eV originate from MQW section 18, where the notations mnH and mnL denote interband excitonic transitions between the mth conduction subband and the nth valence subband of the heavy (H) and light(L) hole characters, respectively. FIG. 3 illustrates the photoreflectance characteristics of the 11 H transition at a wavelength of 1.482 μm and energy of 0.837 eV, and the photoreflectance of the 11 L transition at a wavelength of 1.406 μm and energy of 0.882 eV. Various prior art techniques exist that are also capable of providing information regarding these 11 H and 11 L transitions. In accordance with the present invention, however, the utilization of micro-photoreflectance to scan the entire structure allows for the photoreflectance properties of each layer to be determined. In particular and as shown in FIG. 3, photoreflectance features associated with barriers 22, separate confinement layers 16,24, and InP setback layer 26 are determined by using the micro-photoreflectance arrangement of the present invention. Since barriers 22 and separate confinement layers 16,24 are the same wavelength (i.e., 1.26 μm), a single photoreflectance feature, denoted by the label "A" in FIG. 3, is associated with these layers. This photoreflectance feature exhibits a wavelength of 1.232 μm and an energy of 1.006 eV. The InP setback photoreflectance feature, denoted "B" in FIG. 3, exhibits a wavelength of 0.926 μm and an energy of 1.338 eV.

Since EML structure 10 forms a p-i-n junction 36, as illustrated in FIG. 1 and discussed above, Franz-Keldysh oscillations appear in the photoreflectance measurements between the barrier/SCL peak A and InP setback peak B. Four of the maxima and minima (i.e. "extrema") of these oscillations are denoted by numerals I, II, III and IV in FIG. 3.

Figure 4:
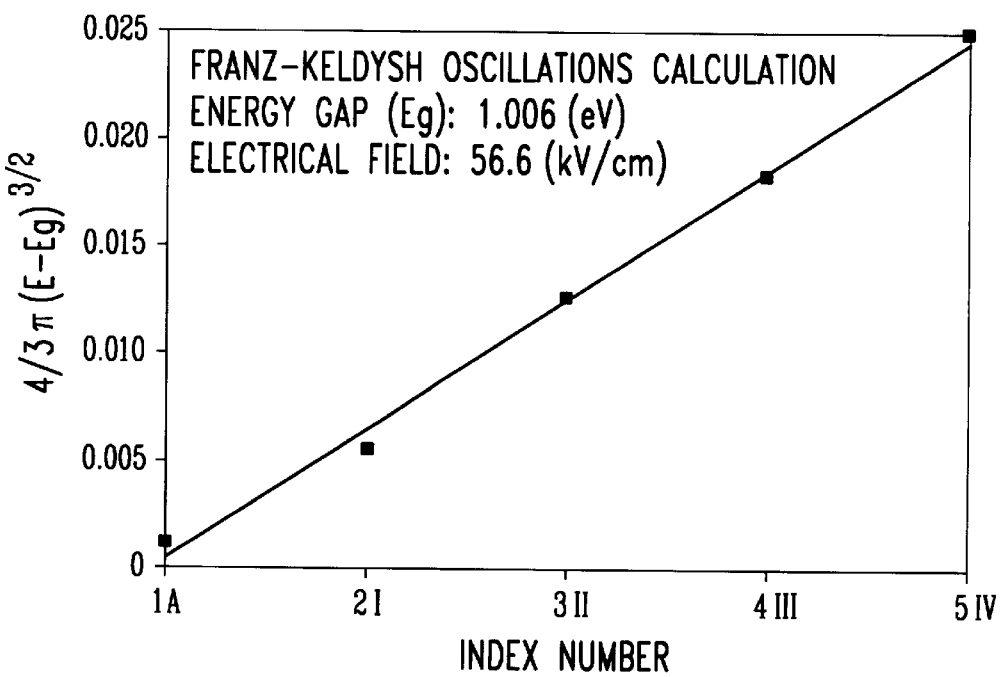
FIG. 4 contains a plot illustrating an electric field calculation based on the Franz-Keldysh oscillations illustrated in the graph of FIG. 3.

The electric field strength of the undoped region comprising MQW section 18, separate confinement layers 16,24 and the undoped portion of InP setback layer 26 can be calculated by applying the following relationship:

$$m\pi = \phi + 4/3[(E_m - E_g)/\hbar\theta]^{3/2}$$

where m is the index of the mth oscillation extrema (the four extrema being denoted I, II, III and IV in FIG. 3) and $\phi$ is an arbitrary phase factor. $E_m$ is the energy of the mth extrema and $E_g$ is the bandgap of the barriers and separate confinement layers. $\hbar\theta$ is the electro-optic parameter:

$$(\hbar\theta)^3 = e^2\hbar^2 F_{dc}^2/2\mu_{II}$$

where $F_{dc}$ is the electric field and $\mu_{II}$ is the reduced interband effective mass in the direction of the field. FIG. 4 is a plot of $4/3\pi[(E_m - E_g)]^{3/2}$ as a function of the extrema index I, II, III and IV. Using this plot, the electric field can be determined, and in this particular case, the electric field has a value of 56.6 kV/cm. Advantageously and in accordance with the present invention, this electric field calculation is derived in a non-destructive manner using the micro-photoreflectance arrangement of the present invention.

Figure 5:
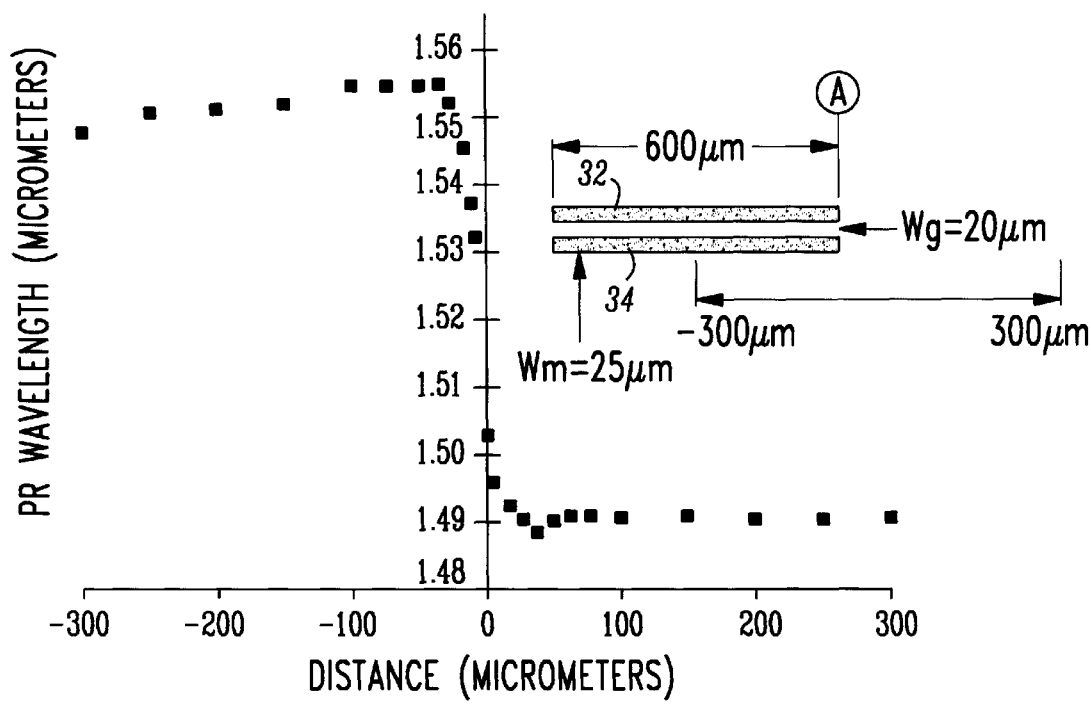
FIG. 5 illustrates the micro-photoreflectance wavelengths of the 11 H excitonic transition as measured from the center of a laser stripe to the planar (modulator) region of the EML structure.

FIG. 5 is a graph containing the micro-photoreflectance wavelengths, associated with the 11 H excitonic transition as shown in FIG. 3. The measurements were obtained from the patterned area of EML device 10, a portion of which is again illustrated in FIG. 5. In particular, the distance across the abscissa of FIG. 5 from –300 micrometers to 0 micrometers represents the micro-photoreflectance measurements obtained from the center of oxide stripes 32,34 to the planar, unpatterned region (extending from 0 micrometers to +300 micrometers. For the exemplary EML device being measured, the width of the oxide stripes ($W_m$) is 25 micrometers and the width of the gap between the stripes ($W_g$) is 20 micrometers. An abrupt transition in the well wavelength from approximately 1.55 micrometers to 1.49 micrometers is seen to occur at location C, the interface between oxide stripes 32,34 and the planar (modulator) region. The longer wavelength of 1.55 micrometers for the patterned (laser) region can be attributed to enhanced growth occurring within stripes 32,34. The relative linearity of wavelength within both regions is an indicator of the uniform quality of the quantum well layers within the EML structure. As with the electric field calculation discussed above, this evaluation of the structure is also non-destructive and yields an indicator of the quality of EML device.

Figure 6:
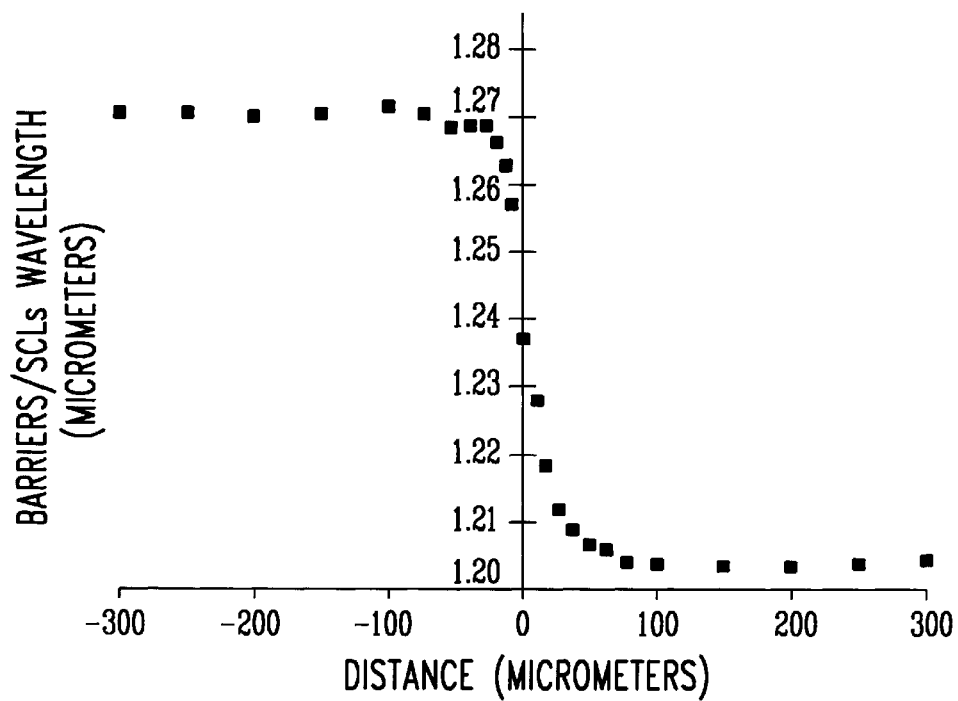
FIG. 6 is a graph of the measured micro-photoreflectance obtained from the barriers/separate confinement layers, as scanned from the laser stripe to the planar area of the EML structure.
Figure 7:
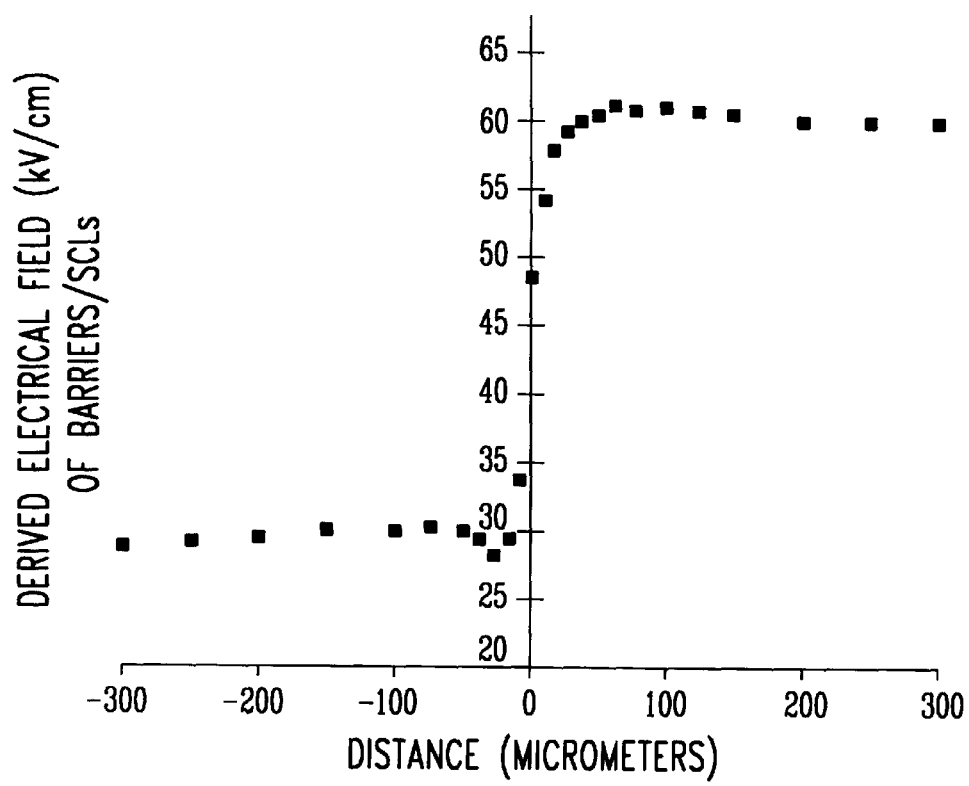
FIG. 7 contains a plot of the electric field as derived from the Franz-Keldysh oscillations following the barriers/separate confinement layers as shown in FIG. 6.

FIG. 6 contains a similar graph, measuring the micro-photoreflectance wavelengths of the barrier/separate confinement layer regions along this same −300 micrometer to +300 micrometer span. Again, there is an abrupt transition (denoted by the letter "D") between the measured wavelength of approximately 1.27 micrometers for the patterned region and 1.20 micrometers for the planar region. This transition thus demonstrates that the InGaAsP composition and layer thicknesses differ for the patterned and planar regions. The derived electric field values (using the above equations) for the structure are plotted in FIG. 7. The lower electric field value of approximately 30 kV/cm for the patterned area (as compared with the value of approximately 60 kV/cm for the planar region) indicates that the layers grown within stripes 32,34 are significantly thicker than the layers deposited in the planar region.

Figure 8:
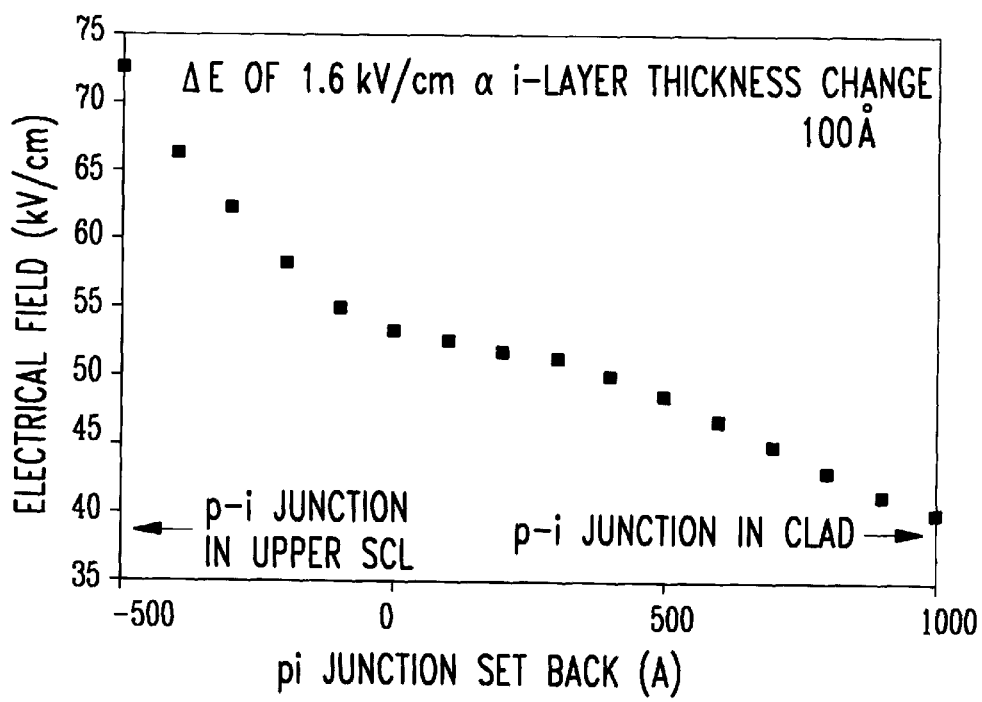
FIG. 8 is a graph illustrating the relationship between the derived electric field and the p-i junction placement in an InGaAsP EML device.

As mentioned above, a significant advantage of the micro-photoreflectance technique of the present invention is the capability of ascertaining the location of p-i junction 36 within the FML structure. In particular, by employing a p-type carrier density of $2 \times 10^{18}$ cm$^{-3}$, an n-type carrier concentration of $1 \times 10^{18}$ cm$^{-3}$ and $1 \times 10^{15}$ cm$^{-3}$ for the intrinsic layer background doping, the thickness of the depletion region can be correlated with the electric field values. FIG. 8 is a graph illustrating the electric field profile as a function of the p-i junction placement relative to the p-type separate confinement layer hetero interface. As shown, from 0 to 1000 Å, p-i junction 36 is found in InP setback layer 26, and from 0 to −500 Å, p-i junction 36 lies within upper separate confinement layer 24. Based upon a comparison of the derived electric field with the thickness of the intrinsic layer obtained by SIMS analyses, a change in the electric field of 1.6 kV/cm has been found to correspond to an intrinsic layer thickness change of 100 Å.

Figure 9:
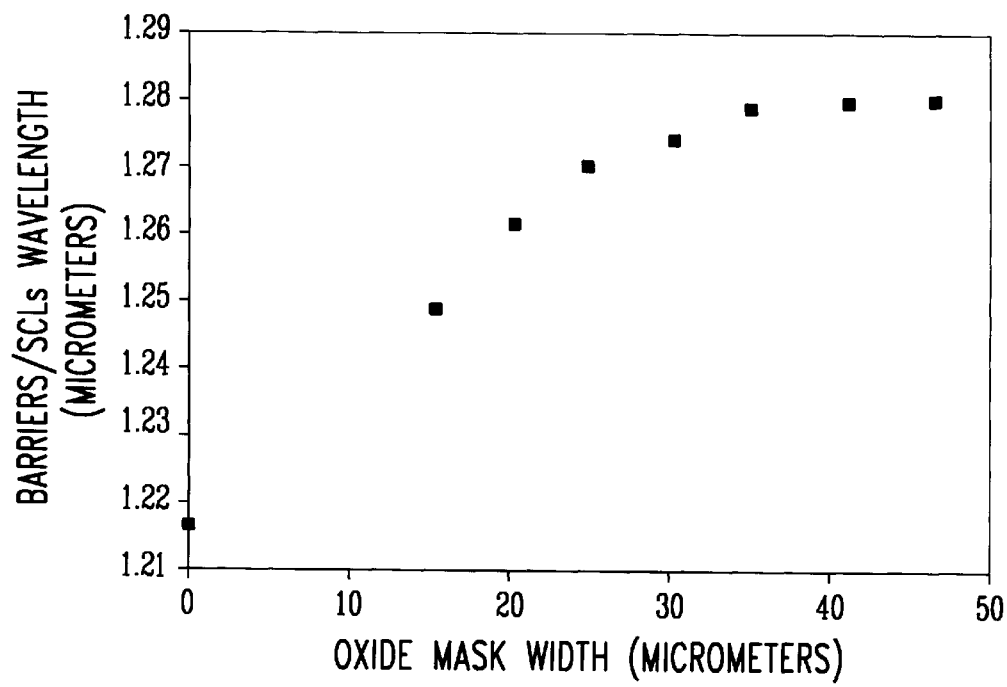
FIG. 9 illustrates the micro-photoreflectance wavelengths from the barriers/separate confinement layers as a function of the silicon dioxide mask width.

FIG. 9 contains a graph illustrating micro-photoreflectance wavelengths obtained in the barrier/separate confinement layer region as a function of changing width of the silicon dioxide mask. The measurements were obtained from the centers of the 600 micrometer oxide stripes 32,34 and the centers of the 20 micrometer gaps. The oxide mask widths were varied from 15 micrometers to 45 micrometers in 5 micrometer increments, as shown in FIG. 9. As shown, the wavelength increases as the oxide mask width increases until $W_m$ reaches about 35 micrometers. The wavelength of 1.28 micrometers is then essentially constant, an indication that the vapor phase diffusion length of the group III species into the barrier region has been exceeded.

Figure 10:
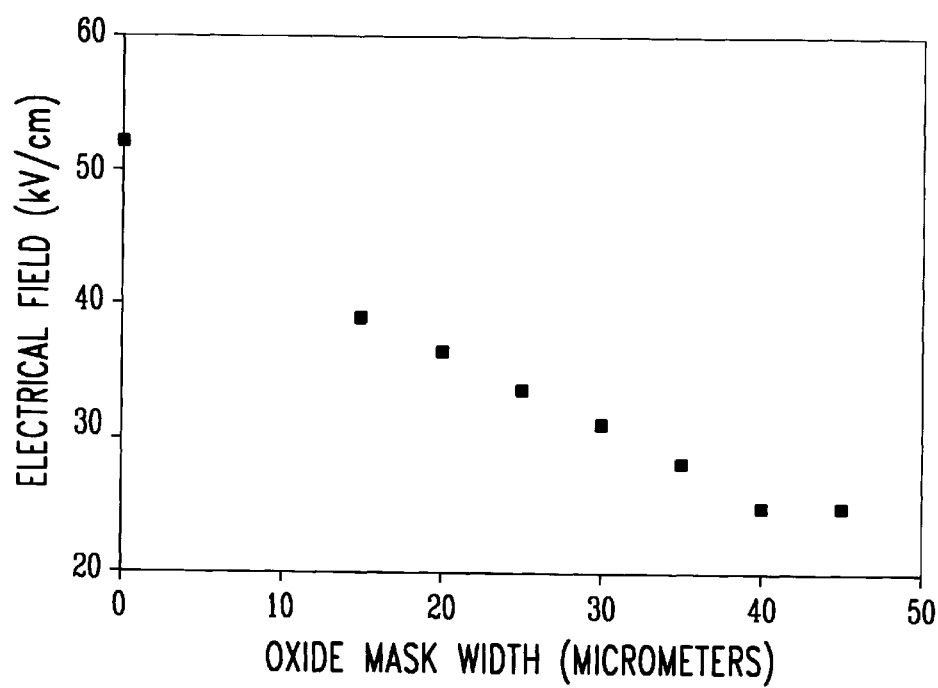
FIG. 10 contains a graph illustrated the derived electric field as a function of the silicon dioxide mask width.

The effect of the oxide mask width on the electric field is illustrated in FIG. 10, which contains a plot of the derived electric field as a function of the oxide mask width. The electric field is shown as decreasing for increasing oxide mask width, until a width of approximately 40 micrometers is reached. After this point, the electric field remains essentially constant at a value of approximately 25 kV/cm.

Figure 11:
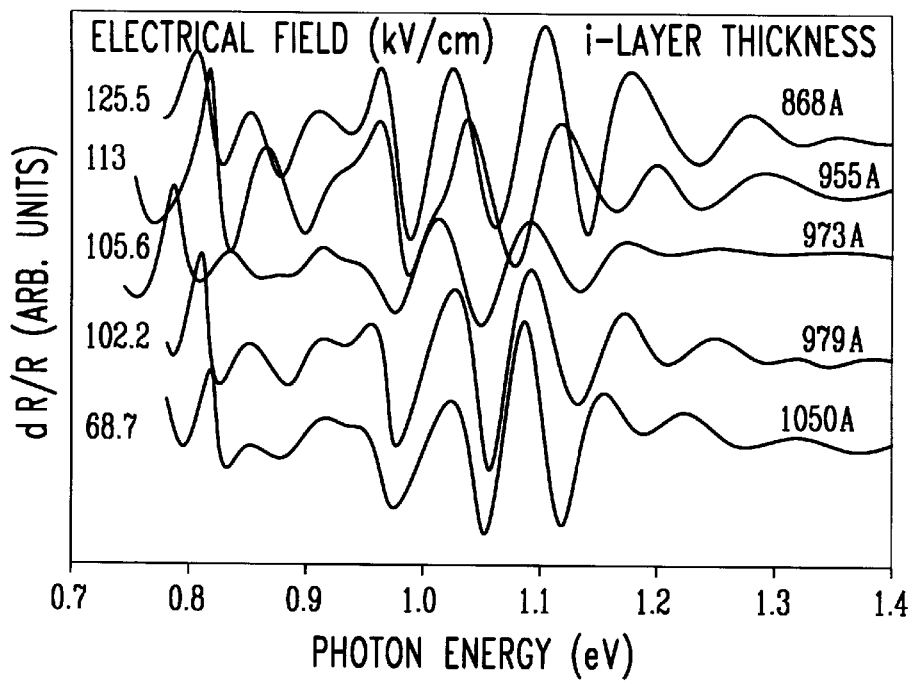
FIG. 11 a graph comparing a set of different micro-photoreflectance measurements obtained for different EML structures.
Figure 12:
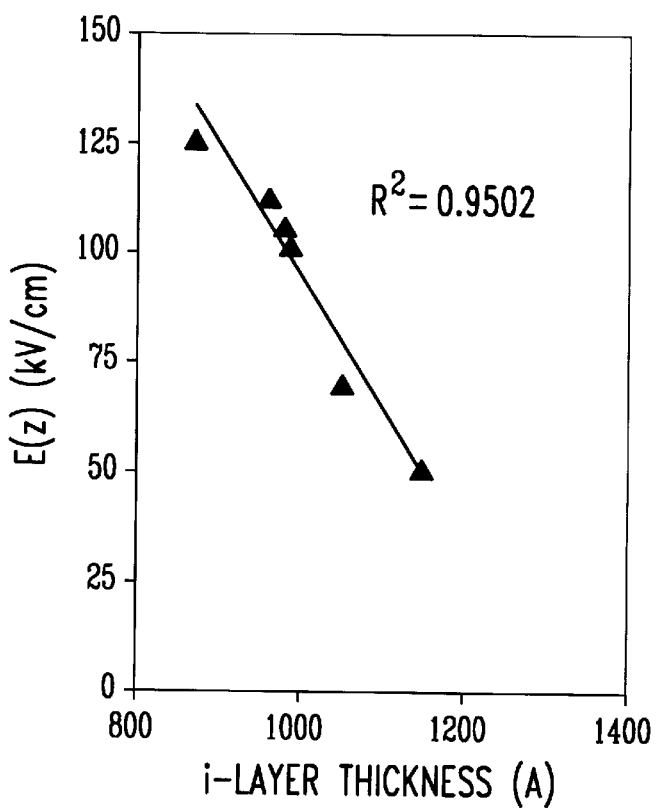
FIG. 12 contains a plot of the derived electric field and p-i junction placement for the set of EML structures associated with the measurements of FIG. 11.

The micro-photoreflectance measurements associated with a set of five different EML devices is shown in FIG. 11. In each instance, the location of the p-i junction is slightly different, as is the derived electric field. These values are obtained, as discussed above, by obtaining the Franz-Keldysh oscillation extrema located beyond the barrier/SCL photoreflectance peak (these extrema being denoted by the numerals I, II, III and IV in each graph of FIG. 11). FIG. 12 contains a plot of the i layer thickness as function of the derived electric field for the five devices of FIG. 10. As shown, a relationship applies to these values, as defined by the Poisson equation.

The micro-photoreflectance technique of the present invention has been found to provide significant data regarding the characteristics of an optoelectronic device without the need to perform destructive tests upon the device. As a result, each optoelectronic wafer may be analyzed as it is being processed, ensuring the quality of each device so produced.

What is claimed is:

1. A method of obtaining physical characteristic data related to a III–V optoelectronic device, the method comprising the steps of:
   a) providing a III–V optoelectronic device, said device including a substrate and a plurality of separate layers, said separate layers being one of n-doped, p-doped and undoped;
   b) providing a monochromatic light source having a predetermined small spot size of approximately 10 micrometers or less;
   c) illuminating a first area of said III–V optoelectronic device of step a) with the small spot size monochromatic light source provided in step b);
   d) recording reflected wavelength information from the illumination of step c);
   e) repeating steps c) and d) along said device so as to collect micro-phtoreflectance information across the plurality of separate layers of said III–V optoelectronic device; and
   f) analyzing the micro-photoreflectance data recorded in step d) to obtain information related to the physical characteristics of said III–V optoelectronic device.

2. The method as defined in claim 1 wherein in performing step d), wavelength information is recorded related to a plurality of Franz-Keldysh oscillations associated with the plurality of separate layers, and in performing step f), an electric field value is derived from the plurality of Franz-Keldysh oscillations.

3. The method as defined in claim 1 wherein in performing step b), a He—Ne laser light source is provided.

4. The method as defined in claim 1 wherein in performing step a) an InGaAsP EML device is provided, said device including a substrate, a lower separate confinement layer, a multiple quantum well structure disposed over the lower separate confinement layer, an upper separate confinement layer, an InP setback layer, and an InGaAsP cap layer, the structure forming a p-I-n device with a p-I junction formed within the upper separate confinement layer.

5. The method as defined in claim 4 wherein in performing step d), wavelength information is recorded related to a plurality of Franz-Keldysh oscillations associated with the barrier and the InP separate confinement layer, and in performing step f), an electric field value is derived from the plurality of Franz-Keldysh oscillations.

6. The method as defined in claim 5 wherein in performing step f) a p-i junction location is derived from the electric field value.

7. The method as defined in claim 3 wherein the He—Ne laser is operated at a wavelength of 6328 Å, operating at a power of approximately 3 mW is provided.

* * * * *